United States Patent [19]

Nishioka et al.

[11] 4,398,811

[45] Aug. 16, 1983

[54] VIEWING-DIRECTION CHANGING OPTICAL SYSTEM

[75] Inventors: Kimihiko Nishioka; Nobuo Yamashita, both of Hachiouji, Japan

[73] Assignee: Olympus Optical Co., Ltd., Tokyo, Japan

[21] Appl. No.: 358,664

[22] Filed: Mar. 16, 1982

Related U.S. Application Data

[63] Continuation of Ser. No. 166,693, Jul. 2, 1980, abandoned.

[30] Foreign Application Priority Data

Jul. 6, 1979 [JP] Japan .................................. 54-85654

[51] Int. Cl.³ .......................... G02B 23/02; A61B 1/00
[52] U.S. Cl. ..................................... 350/506; 350/575; 350/447; 128/7
[58] Field of Search ............... 350/506, 572, 573, 574, 350/575, 447, 286; 128/4, 5, 6, 7

[56] References Cited

U.S. PATENT DOCUMENTS 1,309,478  7/1919  Jenkins ................................. 350/541
1,445,284  2/1923  Bell et al. ............................ 350/559

FOREIGN PATENT DOCUMENTS 229456  8/1904  Fed. Rep. of Germany ...... 350/544

Primary Examiner—Jon W. Henry
Attorney, Agent, or Firm—Cushman, Darby & Cushman

[57] ABSTRACT

A viewing-direction changing optical system comprising an optical fiber bundle, a reflecting means arranged to deflect the optical axis to a direction different from the axis of the optical fiber bundle, and lenses arranged in front and rear (the object side and image side) of the reflecting means, the viewing-direction changing optical system being arranged to change the viewing direction by sliding the reflecting means in the direction of optical axis.

8 Claims, 16 Drawing Figures

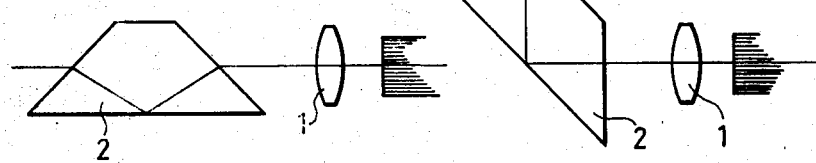
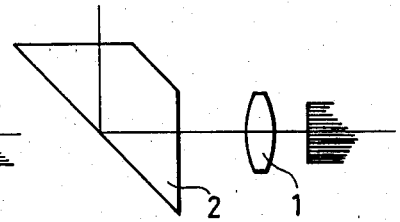
FIG. 1A PRIOR ART
FIG. 1B PRIOR ART
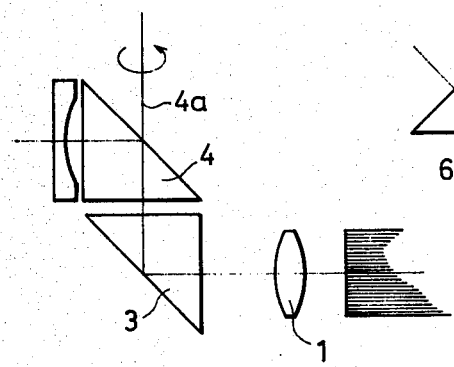
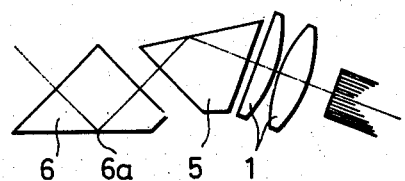
FIG. 2 PRIOR ART
FIG. 3 PRIOR ART
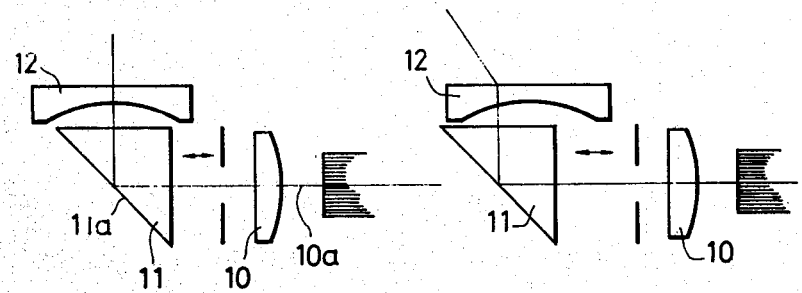
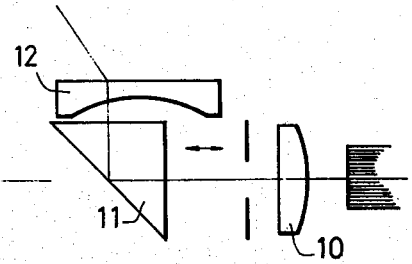
FIG. 4A
FIG. 4B

VIEWING-DIRECTION CHANGING OPTICAL SYSTEM

This is a continuation, of application Ser. No. 166,693 filed July 2, 1980 now abandoned.

BACKGROUND OF THE INVENTION

1. Field of the Invention

The present invention relates to a viewing-direction changing optical system for long and slender image-transmission systems such as endoscopes.

2. Description of the Prior Art

When observing the inside of body cavity by an endoscope in which an optical fiber bundle is used, it is possible to observe in various directions in the body cavity by bending the distal end of endoscope. However, in such observing method to bend the distal end of endoscope, the observing directions are limited and there occur some directions in which observation is impossible. Moreover, when it is impossible to bend the endoscope itself as in case of an inflexible endoscope, it is possible to observe in one direction only. Therefore, in order to enable to observe in a wide range, a viewing-direction changing optical system is required. As viewing-direction changing optical systems, such optical systems as shown in FIGS. 1 through 3 are known. The optical system shown in FIGS. 1A and 1B is arranged as follows. That is, a roof prism 2 is arranged in front of objective 1 of endoscope. The observing direction is changed from the forward viewing direction to the side viewing direction by rotating the roof prism 2 from the position shown in FIG. 1A to the position shown in FIG. 1B. The optical system shown in FIG. 2 is arranged as follows. That is, two right-angled prisms 3 and 4 are arranged in front of objective 1. One prism 3 is fixed while the other prism 4 is rotated round the axis 4a (when a concave lens is arranged in front of prism 4 as shown in FIG. 2, the prism 4 is rotated integrally with the concave lens). Thus, it is possible to observe in a wide range of viewing directions. The optical system shown in FIG. 3 is arranged as follows. That is, two prisms 5 and 6 are arranged in front of objective 1. Out of those prisms, the prism 6 is rotated round the axis 6a. Thus, it is possible to observe in various directions.

Known viewing-direction changing optical systems explained in the above are all arranged to change the viewing direction by rotating the prism or one of prisms arranged in front of objective and, therefore, they need a large space and complicated mechanism for rotation of prism. Consequently, the distal end becomes large and this is not desirable for endoscopes.

SUMMARY OF THE INVENTION

It is, therefore, a primary object of the present invention to provide a viewing-direction changing optical system for long and slender image-transmission systems for which disadvantages of known viewing-direction changing optical systems are eliminated.

Another object of the present invention is to provide a viewing-direction changing optical system for long and slender image-transmission systems which is capable also of focusing the objective at the same time as changing of viewing direction.

BRIEF DESCRIPTION OF THE DRAWINGS

FIGS. 1 through 3 respectively show sectional views of known viewing-direction changing optical systems;

FIGS. 4A and 4B respectively show sectional views of Embodiment 1 of the viewing-direction changing optical system according to the present invention;

DETAILED DESCRIPTION OF THE PREFERRED EMBODIMENTS

Figure 5A:
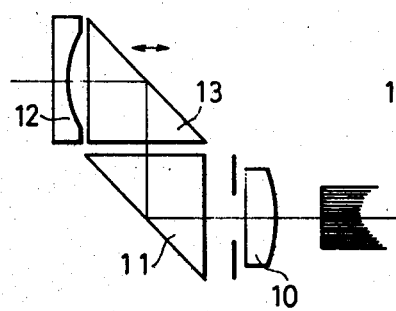
FIGS. 5A and 5B respectively show sectional views of Embodiment 2 of the present invention.

Now, the contents of the present invention are explained referring to the respective embodiments shown on the drawings. FIGS. 4A and 4B show the optical system according to Embodiment 1 of the present invention in which a right-angled prism 11 and concave lens 12 are arranged in front (the object side) of a convex lens 10 (this may be a positive lens group comprising a plural number of lenses though only one lens is shown in this figure) and in which the convex lens 10 and concave lens 12 constitute the objective. When the relative positions of prism and lenses in this optical system are as shown in FIG. 4A, rays passed the concave lens 12 along its optical axis and reflected by the surface 11a of prism 11 pass the convex lens 10 along its optical axis 10a. When the prism 11 in this optical system is kept fixed and concave lens 12 is moved right-hand as viewed in the figure, rays from the left oblique direction in the figure are reflected by the prism 11 and pass the convex lens 10 along its optical axis 10a. Therefore, it is possible to observe the left oblique direction in respect to the sideviewing direction. When the concave lens 12 is moved leftward from the position shown in FIG. 4A on the contrary to the above, it is possible to observe the right oblique direction.

When the concave lens 12 in this optical system is kept fixed and prism 11 is moved in the direction along the optical axis 10a of convex lens 10, i.e., in the direction shown by the arrowhead in FIG. 4A, and comes to the position shown in FIG. 4B, rays from the left oblique direction in the figures are reflected by the prism 11 and pass the convex lens 10 along its optical axis 10a. That is, by sliding the prism 11, it is also possible to change the viewing direction to the sideviewing direction shown in FIG. 4A, oblique-viewing direction shown in FIG. 4B and so forth. Also in this case, the moving direction of prism 11 is not limit to the above-mentioned direction, i.e., from the position shown in FIG. 4A toward the direction in which the prism 11 moves away from the convex lens 10. It is also possible to move the prism 11 in the opposite direction, i.e., from the position shown in FIG. 4A toward the direction in which the prism 11 approaches the convex lens 10 and to observe the right oblique direction in respect to the side viewing direction as well as the left oblique direction shown in FIG. 4B. Instead of moving the prism 11 only, the viewing direction may be changed by integrally moving the prism 11 and lens 10.

In the above-mentioned method to move the prism 11, it is possible to carry out focusing of objective at the same time as changing of viewing direction as described later.

Figure 5B:
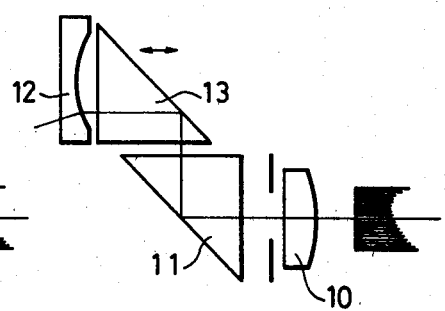

FIGS. 5A and 5B show Embodiment 2 of the present invention in which another right-angled prism 13 is arranged in addition to the right-angled prism 11 and the concave lens 12 is arranged in the direction different from the case of Embodiment 1. This optical system is arranged to change the viewing direction by integrally moving the prism 13 and concave lens 12 in the direction parallel with the optical axis of convex lens 10. That is, when the prism 13 and concave lens 12 are moved leftward from the position shown in FIG. 5A to the position shown in FIG. 5B, it is possible to change the observing direction from the forward-viewing direction shown in FIG. 5A to the lower-oblique viewing direction shown in FIG. 5B. Also in case of this embodiment, it is also possible to observe the upper-oblique direction as viewed in the figure by moving the prism 13 and concave lens 12 rightward from the position shown in FIG. 5A. It is also possible to fix the concave lens 12 and to move the prism 13 only. Besides, it is also possible to fix both of concave lens 12 and prism 13 and to move the prism 11 or to integrally move the prism 11 and convex lens 10. In case of this embodiment, the optical path length from the convex lens 10 to the concave lens 12 changes in the method to move the prism 13 only, method to move the prism 11 only and method to integrally move the prism 11 and convex lens 10 and, therefore, it is possible to focus the objective at the same time as changing of viewing direction.

Figure 6A:
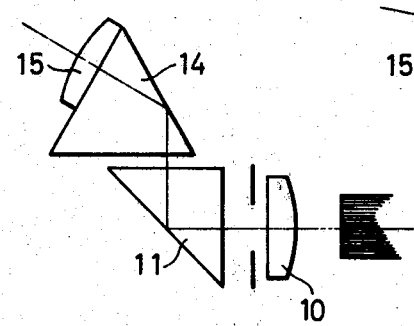
FIGS. 6A and 6B respectively show sectional views of Embodiment 3 of the present invention.
Figure 6B:
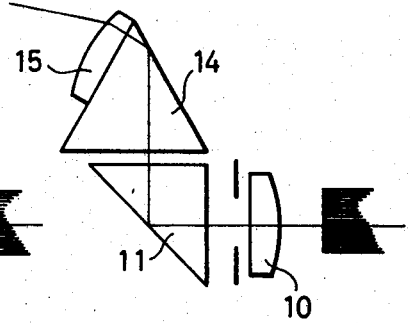

FIGS. 6A and 6B show Embodiment 3 in which the idea of the present invention is applied to an oblique-viewing type optical system. This embodiment is arranged to change the viewing direction by integrally moving the prism 14 for oblique viewing and convex lens 15, which is arranged in front of prism 14, from the position shown in FIG. 6A to the position shown in FIG. 6B in the direction parallel with the optical axis of convex lens 10.

Figure 7A:
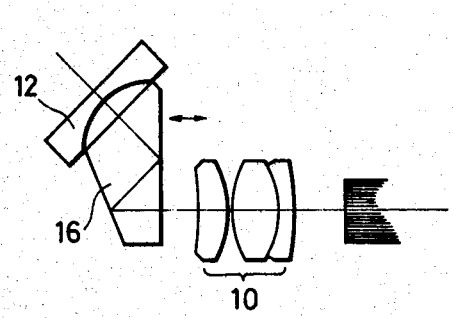
FIGS. 7A and 7B respectively show sectional views of Embodiment 4 of the present invention.
Figure 7B:
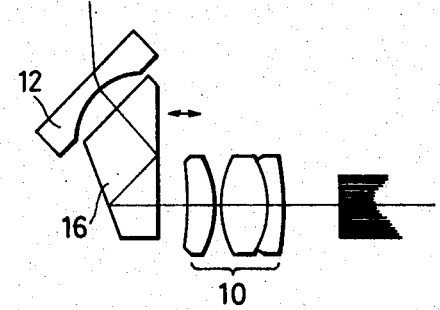

Further, FIGS. 7A and 7B show Embodiment 4 in which the idea of the present invention is applied also to an oblique-viewing type optical system. In case of this embodiment, it is possible to change the viewing direction by moving the prism 16 for oblique viewing from the position shown in FIG. 7A to the position shown in FIG. 7B in the direction parallel with the optical axis of convex lens 10.

Figure 8:
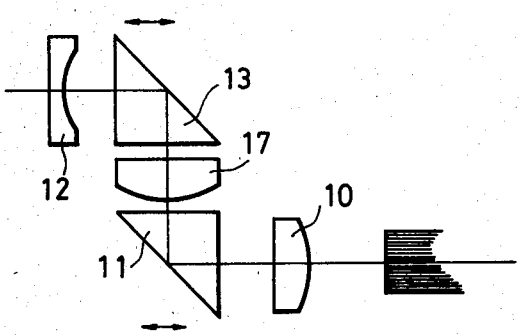
FIG. 8 shows sectional view of Embodiment 5 of the present invention.

FIG. 8 shows Embodiment 5 of the present invention in which a positive lens 17 (or a positive lens group) is arranged between the prism 11 and prism 13 of the optical system arranged as shown in FIGS. 5A and 5B. When the prism 13 in this optical system is moved in the direction of arrowhead, it is possible to change the viewing direction and, at the same time, to focus the objective. It is also possible to change the viewing direction and to focus the objective when the prism 13 and lens 17 are moved integrally. When the prism 13 and lens 12 are integrally moved in the direction of arrowhead, it is possible to change the viewing direction. The viewing direction can be changed also when the prism 13, lens 12 and lens 17 are moved integrally. Besides, when only the prism 11 in the optical system shown in FIG. 8 is moved in the direction of arrowhead, it is possible to change the viewing direction and to focus the objective at the same time. Furthermore, it is also possible to change the viewing direction and to focus the objective when the prism 11 and lens 17 are moved integrally, when the prism 11 and lens 10 are moved integrally and when the prism 11, lens 10 and lens 17 are moved integrally.

As described hitherto based on the respective embodiments, the viewing-direction changing optical system according to the present invention comprises at least one reflecting means (for example, the prism 11 and prism 13) arranged between a first lens group (for example, the lens 12) and a second lens group (for example, the lens 10). Said reflecting means may include a lens as, for example, the lens 17 in Embodiment 5. In the viewing-direction changing optical system arranged as above, the viewing direction is changed by relatively shifting the optical axis of the first lens group and optical axis of he second lens group.

For the above-mentioned viewing-direction changing, the reflecting means (for example, the prism 13) and the first lens group (for example, the lens 12) may be integrally moved as in case of Embodiment 2 or the reflecting means (for example, the prime 13) and the second lens group (for example, the lens 10) may be integrally moved as described in relation to Embodiment 1.

When the above-mentioned viewing-direction changing optical system according to the present invention is used, it is almost always possible to carry out focusing of objective, at the same time as sliding a part of optical system, by utilizing the change in the relative positions of elements constituting the optical system to be caused at the time of sliding. In case of endoscopes, parallax occurs between the objective and illuminating optical system when observing an object at a close distance. Besides, when a forceps means is to be used, the forceps means comes to a position deviated from the optical axis of objective. When, however, the optical system according to the present invention is used, it is possible to easily solve the problem of parallax between the objective and illuminating system and to easily bring the forceps means to the center of field. Moreover, it is also possible to arrange so that focusing of objective is carried out at the same time as changing of viewing direction.

Figure 9:
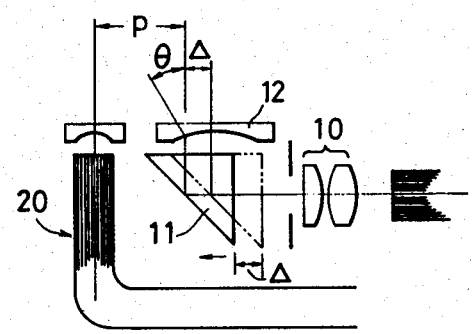
FIGS. 9 through 11 respectively show explanatory figures illustrating the states when changing of viewing direction and focusing of objective are carried out at the same time.
Figure 10:
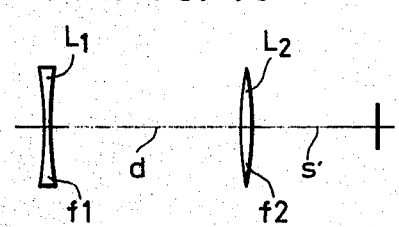
Figure 11:
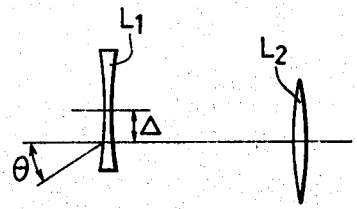

Now, the fact that focusing and elimination of parallax can be carried out at the same time is explained below by using the paraxial theory and referring to FIGS. 9 through 11. FIG. 9 shows a viewing-direction changing optical system having an illuminating optical system 20 while FIGS. 10 and 11 show the lenses only. In FIGS. 10 and 11, the lenses are shown as thin lenses. FIG. 10 shows the state that the optical axes of both lenses are aligned with each other while FIG. 11 shows the state that the optical axes of both lenses are shifted from each other. As shown in FIG. 10, the reference symbol $f_1$ represents the focal length of front lens group $L_1$ (the concave lens 12 shown in FIG. 9) constituting the imaging lens system (which consists of a negative lens group and a positive lens group), reference symbol $f_2$ represents the focal length of rear lens group $L_2$ constituting the imaging lens system, reference symbol d represents the distance between the front and rear lens groups, and reference symbol $s'$ represents the distance from the rear lens group $L_2$ to the image surface. When the prism 11 is moved to the left as shown by the arrowhead in FIG. 9 by the value $\Delta$, the distance between the front lens group $L_1$ and rear lens group $L_2$ increases by $\Delta$. When reference symbol $s_1$ represents the distance to an object at long distance, reference symbol $s_2$ represents the distance to an object at short distance, reference symbol p represents the value of parallax and reference symbol $\theta$ represents the value of change in viewing direction, the relation expressed by the following equation (1) is obtained when parallax is eliminated.

$$p = s_2 \cdot \theta \tag{1}$$

where, $$s_1 > s_2$$

When the prism is moved by $\Delta$, rays passed the front lens group $L_1$ at the point shifted by $\Delta$ from the center thereof pass the center of rear lens group $L_2$ as shown in FIG. 9 or 11 and, therefore, the viewing direction changes by $\theta$ shown below.

$$\theta = \Delta / |f_1| \tag{2}$$

In case that the end face of optical fiber bundle and rear lens group are arranged in such positions where the objective is focused on an object at long distance and they are fixed in those positions, the distance between the front lens group and rear lens group increases by $\Delta$ when the viewing direction is changed by moving the prism by $\Delta$ in order to observe an object at short distance. In case that the position of image formed when the distance between the front and rear lens groups increases by $\Delta$ is the same as the position of image formed when the objective is focused on the object at long distance, it is possible to carry out focusing and changing of viewing direction at the same time. This is achieved on condition that the distance $s_1'$ from the rear lens group to the image when the objective is focused on the object at long distance is made equal to the distance $s_2'$ from the rear lens group to the image when the objective is focused on the object at short distance. Therefore, the relation expressed by the following equations (3) is obtained.

$$\frac{1}{s'_1} = \frac{1}{f_2} - \frac{\frac{1}{f_1} - \frac{1}{s_1}}{d\left(\frac{1}{f_1} - \frac{1}{s_1}\right) - 1} \tag{3}$$

$$\frac{1}{s'_2} = \frac{1}{f_2} - \frac{\frac{1}{f_1} - \frac{1}{s_2}}{(d + \Delta)\left(\frac{1}{f_1} - \frac{1}{s_2}\right) - 1}$$

$$s'_1 = s'_2$$

Besides, the focal length f of the imaging lens system as a whole is given by the following equation (4).

$$\frac{1}{f} = \frac{1}{f_1} + \frac{1}{f_2} - \frac{d}{f_1 f_2} \tag{4}$$

Therefore, to carry out focusing and elimination of parallax at the same time when $s_1$, $s_2$, p, and f are given, it is all right when $f_1$, $f_2$, d, $\theta$ and $\Delta$ are obtained by solving the simultaneous equations (1) through (4) by taking $f_1$, $f_2$, d, $\theta$ and $\Delta$ as unknown quantities. In other words, five unknown quantities are to be obtained by four equations. Therefore, it is possible to decide one of unknown quantities to an arbitrary value. For example, the distance between the front and rear lens groups should not be made too large because the hard distal end of endoscope becomes long if said distance is large. Therefore, values of said distance suitable for actual use are limited to some extent. Besides, the value of movement $\Delta$ of prism should not be made large due to the same reason as described in the above and should not be made too small because it becomes impossible to accurately change the viewing direction if $\Delta$ is too small. Therefore, values of $\Delta$ are also limited considerably. When any one of five parameters is decided to a particular value within the range available for that parameter, it is possible to obtained the other four parameters by solving the afore-mentioned simultaneous equations. When the values of respective parameters are obtained as above and when all of those values of parameters are suitable for practical use, it is possible to obtain an optical system which can be used actually and with which changing of viewing direction and focusing can be carried out at the same time. An example of the viewing-direction changing optical system according to the present invention (values of parameters $s_1$, $s_2$ ... $\Delta$) obtained as above is shown below.

When given parameters are:

$$s_1 = \infty, \, s_2 = 20 \text{ mm}, \, p = 3 \text{ mm}, \, f = 3 \text{ mm}.$$

The others are:

$$f_1 = -3.52 \text{ mm}, \, f_2 = 3.46 \text{ mm}, \, d = 4 \text{ mm}, \, \theta = 8.5°,$$
$$\Delta = 0.52 \text{ mm}$$

For the optical system arranged to change the viewing direction and carry out focusing at the same time which is described hitherto based on FIGS. 9 through 11, it is so arranged to move the prism 11 only. As described before, it is also possible to change the viewing direction and carry out focusing at the same time by integrally moving the prism 11 and rear lens group 10. When the prism 11 and rear lens group 10 are moved integrally, the distance d between the front lens group 12 and rear lens group 11 remains unchanged and only the distance from the rear lens group to the image increases by $\Delta$. This method is similar to the case that lens systems in general are focused by advancing the lens system as a whole. That is, when $s_1$, $s_2$, p and f are given, it is possible to obtain $f_1$, $f_2$, d, $\Delta$, $\theta$ and $f_F$ by solving the simultaneous equations (5) through (6) shown below.

$$p = s_2 \cdot \theta \tag{5}$$

$$\theta = \Delta / |f| \tag{6}$$

$$\Delta = f^2 \left( \frac{1}{s_2 + f_F} - \frac{1}{s_1 + f_F} \right) \tag{7}$$

$$f_F = \frac{-1}{\frac{1}{f_1} - \frac{1}{d - f_2}} \tag{8}$$

$$\frac{1}{f} = \frac{1}{f_1} + \frac{1}{f_2} - \frac{d}{f_1 f_2} \tag{9}$$

In the above equations, reference symbol $f_F$ represents the front focal point of objective lens system and its value is positive when the front focal point exists in the inside of the lens system.

As six unknown quantities are to be obtained from five equations, decision of any one of them to a particular value enables to decide all the other unknown quantities in the same way as the afore-mentioned case shown in FIGS. 9 through 11. An example of the viewing-direction changing optical system according to the present invention obtained as above is shown below.

When given parameters are:

$s_1 = \infty$, $s_2 = 20$ mm, $f = 2.915$ mm, $p = 2.82$ mm,

The others are:

$f_1 = -3$ mm, $f_2 = 3$ mm, $d = 3.0873$ mm, $\theta = 8°03'$,
$\Delta = 0.423$ mm, $f_F = 0.0848$ mm As it is evident from the explanation given hitherto, in case of the viewing-direction changing optical system according to the present invention, it is possible to provide an optical system for which it is possible to eliminate parallax and to carry out focusing at the same time as changing of viewing direction. In case of the first method shown in FIGS. 9 through 11 in which the prism 11 is moved, focusing is made possible by varying the optical path length between the front and rear lens groups arranged in front and rear of prism 11. In case of the second method, focusing is made possible by integrally moving the prism and rear lens group and thereby varying the distance between the rear lens group and position of image. However, the way for focusing at the same time as changing of viewing direction is not limited to the abovementioned methods. It is also possible to attain the same purpose by further dividing the rear lens group into two lens groups and by moving either of those groups together with the prism. In other words, it is possible to carry out focusing at the same time as changing of viewing direction when the relative positions of optical elements constituting the optical system is varied by changing the position of reflecting means such as a prism or by simultaneously changing the positions of such reflecting means and other optical element or elements.

As explained in detail in the above and it is evident from the examples shown in the above, the viewing-direction changing optical system according to the present invention enables to change the viewing direction by a simple method to move the prism only or to integrally move the prism and a part of lenses only. Therefore, the optical system according to the present invention does not require a large space unlike the known viewing-direction changing optical systems, and moreover, the optical-element moving means and so forth become simple. Besides, the present invention has further advantageous effects. For example, it enables to arrange the optical system so that focusing is carried out at the same time as changing of viewing direction.

Description so far is made based on the case that the viewing direction is changed by providing a reflecting means such as a prism between the lenses constituting the objective (between the negative and positive lenses) and moving said reflecting means. However, it is also possible to apply the idea of the present invention to other portions, for example, to a portion between relay lenses of an inflexible endoscope.

We claim:

1. In an endoscope, a viewing-direction changing optical system comprising at least one reflecting means arranged for the purpose of deflecting the optical axis to a direction different from the axis of said endoscope, a first lens group arranged on the object side of said reflecting means, and a second lens group arranged on the image side of said reflecting means, said viewing-direction changing optical system being arranged to relatively displace the optical axis of said first lens group and optical axis of said second lens group, the optical axis of said endoscope from said reflecting means to said first lens group being adapted to still extend through said first lens group when said reflecting means and first lens group are relatively displaced.

2. A viewing-direction changing optical system according to claim 1, in which said first lens group is arranged to be movable in the direction perpendicular to the optical axis thereof.

3. A viewing-direction changing optical system according to claim 1, in which said reflecting means is arranged to be movable in the direction of the optical axis of said endoscope.

4. In a long and slender image-transmission system a viewing-direction changing optical system comprising at least one reflecting means arranged for the purpose of deflecting the optical axis to a direction different from the axis of the image-transmission system, a first lens group arranged on the object side of said reflecting means, and a second lens group arranged on the image side of said reflecting means, said viewing-direction changing optical system being arranged to relatively displace the optical axis of said first lens group and optical axis of said second lens group, the axis of said image-transmission system from said reflecting means to said first lens group being adapted to still extend through said first lens group when said reflecting means and first lens group are relatively displaced, said first lens group and said reflecting means being arranged to be integrally movable in the direction of the optical axis of said image-transmission system.

5. A viewing-direction changing optical system according to claim 1, in which at least one of said reflecting means and said second lens group are arranged to be integrally movable in the direction of the optical axis of said endoscope.

6. A viewing-direction changing optical system according to claim 1, in which said reflecting means is arranged to deflect the optical axis to the direction perpendicular to the optical axis of said endoscope.

7. In a long and slender image-transmission system a viewing-direction changing optical system comprising at least one reflecting means arranged for the purpose of deflecting the optical axis to a direction different from the axis of the image-transmission system, a first lens group arranged on the object side of said reflecting means, said viewing-direction changing optical system being arranged to relatively displace the optical axis of said first lens group and optical axis of said second lens group, the axis of said image-transmission system from said reflecting means to said first lens group being adapted to still extend through said first lens group when said reflecting means and first lens group are relatively displaced, and said reflecting means being arranged to move along the optical axis in parallel with the optical axis of said image-transmission system.

8. A viewing-direction changing optical system according to claim 4, in which said reflecting means is arranged to deflect the optical axis to a direction oblique to the optical axis of said image-transmission system.

* * * * *